United States Patent
van Dort et al.

(10) Patent No.: US 10,098,992 B2
(45) Date of Patent: Oct. 16, 2018

(54) HEART SUPPORT DEVICE

(71) Applicant: STICHTING KATHOLIEKE UNIVERSITEIT, Nijmegen (NL)

(72) Inventors: Daniël Immanuel Michaël van Dort, Nijmegen (NL); Harry Suryapranata, Zwolle (NL); Paul Frederik Gründeman, Bilthoven (NL); Jakob Roelf Lahpor, Kanata (CA)

(73) Assignee: Stichting Katholieke Universiteit, Nijmegen (NL)

( * ) Notice: Subject to any disclaimer, the term of this patent is extended or adjusted under 35 U.S.C. 154(b) by 0 days.

(21) Appl. No.: 15/322,459

(22) PCT Filed: Jun. 30, 2015

(86) PCT No.: PCT/EP2015/064836
§ 371 (c)(1),
(2) Date: Dec. 28, 2016

(87) PCT Pub. No.: WO2016/001218
PCT Pub. Date: Jan. 7, 2016

(65) Prior Publication Data
US 2017/0136162 A1    May 18, 2017

(30) Foreign Application Priority Data

Jun. 30, 2014   (EP) .................................... 14174988

(51) Int. Cl.
*A61M 1/10* (2006.01)
*A61M 1/12* (2006.01)

(52) U.S. Cl.
CPC ........ *A61M 1/1074* (2014.02); *A61M 1/1006* (2014.02); *A61M 1/1086* (2013.01); *A61M 1/122* (2014.02); *A61M 2205/0216* (2013.01); *A61M 2230/005* (2013.01); *A61M 2230/06* (2013.01)

(58) Field of Classification Search
CPC .. A61M 1/1074; A61M 1/1006; A61M 1/122; A61M 1/1086; A61M 2205/0216; A61M 2230/005; A61M 2230/06
See application file for complete search history.

(56) References Cited

U.S. PATENT DOCUMENTS

| | | | |
|---|---|---|---|
| 5,139,517 A | 8/1992 | Corral | |
| 5,192,314 A | 3/1993 | Daskalakis | |
| 6,406,422 B1* | 6/2002 | Landesberg | A61M 1/1072 600/17 |
| 9,220,824 B2* | 12/2015 | Wildhirt | A61M 1/1008 |
| 2005/0015109 A1* | 1/2005 | Lichtenstein | A61B 17/0057 606/200 |

(Continued)

FOREIGN PATENT DOCUMENTS

WO  PCT/US2010/044429    2/2011

*Primary Examiner* — Catherine Voorhees
(74) *Attorney, Agent, or Firm* — Lindsey A. Auerbach; Catherine Schultz; N.V Nederlandsch Octrooibureau (57) ABSTRACT

Heart support device for circulatory assistance, with an internal member (6) to be disposed inside a heart lumen (13) and having a dynamic volume body. The internal member (6) has a substantially stiff wall strengthening portion (8) arranged to engage an inner wall surface (12*a*) of the heart (10) in operation and a dynamic member (9) that is inflatable to assist pumping action of the heart (10).

18 Claims, 9 Drawing Sheets

(56) References Cited

U.S. PATENT DOCUMENTS

| | | | |
|---|---|---|---|
| 2006/0167334 A1* | 7/2006 | Anstadt | A61M 1/106 600/17 |
| 2008/0146873 A1* | 6/2008 | Adams | A61B 1/303 600/104 |
| 2009/0264989 A1* | 10/2009 | Bonhoeffer | A61F 2/2412 623/1.26 |
| 2013/0184515 A1* | 7/2013 | Ovil | A61M 1/1086 600/17 |
| 2015/0142049 A1* | 5/2015 | Delgado | A61B 17/0057 606/216 |

* cited by examiner

HEART SUPPORT DEVICE

FIELD OF THE INVENTION

The present invention relates to a heart support device, in particular to an intraventricular balloon type pump for circulatory assistance.

PRIOR ART

US patent publication U.S. Pat. No. 6,406,422 discloses a ventricular assist apparent comprising an inflatable balloon to be inserted into a ventricular cavity through a heart wall thereof. The balloon may be expanded and contracted in cadence with normal functioning of a failing heart.

US patent publication US 2013/184515 discloses an intraventricular balloon device. The device comprises a slender flexible catheter with a proximal end and a distal end. An inflatable balloon is provided near the distal end. The balloon is compactly folded onto an outer surface of the catheter in its deflated state allowing entry into e.g. the left ventricle. The (further free floating) balloon can be brought into its inflated state to displace a residual volume of blood from the ventricle. The device may further comprise a second inflatable balloon mounted on the catheter, the second balloon being arranged to be lodged within e.g. the descending aorta.

International patent publication WO 2011/017440) discloses a heart access system and placement device to gain access to an interior of a heart by implanting a port assembly therein. Embodiments of a port assembly comprise a plug having two fixation members disposed on opposite ends thereof that are operable to engage an inner and outer wall surface of a heart. Further embodiments of a port assembly may comprise two discs disposed on opposite ends of a port. The disclosed discs and fixation members are flexible, expandable and/or collapsible.

SUMMARY OF THE INVENTION

The present invention seeks to provide an improved heart support device that can be implanted through a non-invasive procedure as well as a minimally invasive surgery and which is particularly suitable for treating cardiogenic shock and/or chronic heart failure due to a weakened heart wall e.g. as a result of ischemia or post ischemic damage.

According to the present invention, a heart support device of the type defined in the preamble is provided, comprising an internal member to be disposed inside a heart lumen and having a dynamic volume body. The internal member is provided with a substantially stiff wall strengthening portion arranged to engage an inner wall surface of the heart in operation and where a dynamic member is provided that is inflatable to assist pumping action in the heart, thereby providing circulatory assistance.

The heart support device of the present invention reduces known mortality rates associated with patients suffering from reduces cardiac output as a result of a weakened heart wall. The heart support device both mechanically stabilises ischemic cardiac tissue or ventricular aneurysm therefore avoiding the genesis or worsening of a ventricular aneurysm over time as well as providing circulatory assistance to ventricular contraction, thereby compensating for a certain level of heart failure in a patient.

In an embodiment the heart support device further comprises an external shell element having a support surface of a (substantially) rigid material, and being arranged to engage an outer wall surface of the heart. The external shell element is configured to prevent excessive protrusion of e.g. an aneurysm in a heart wall during changing pressure levels inside the heart lumen.

In an embodiment, the wall strengthening portion is expandable, which allows the wall strengthening portion to conform to the inner wall surface of the heart, thereby providing a snug engagement therewith. The expandable wall strengthening portion has the advantage that it follows the inner wall surface when inflated for providing a continuous and distributed support to the inner wall surface with a minimum of localised pressure points.

In an embodiment the wall strengthening portion comprises an inflatable cup shaped body, so that the wall strengthening portion can be conveniently expanded by supplying a gas or fluid thereto and to attain the snug and conformal engagement with e.g. an apex portion of a ventricle.

In an embodiment, the internal member further comprises one or more positioning members for firmly affixing the position and orientation of the heart support device within the heart. When providing circulatory assistance, the heart support device is subjected to repetitive heart movement and muscle contractions. In particular, the one or more positioning members prevent that the heart support device changes its position or orientation during many cardiac cycles.

In order to provide firm fixation, in an embodiment the one or more positioning members may each comprise an arc shape for conformal engagement with an internal structure and inner surface of the heart lumen. This embodiment provides a distributed fixation force by the one or more arc shaped positioning members, minimizing possible irritation of the inner wall surface of the heart lumen yet preventing dislodgement of the heart support device during many pumping cycles.

In an advantageous embodiment the one or more positioning members comprise a tubular shape, allowing a gas or fluid to pass there through for inflating and deflating the dynamic volume body, e.g. the inflatable dynamic member. The one or more positioning members may also be used to bring the wall strengthening portion from a collapsed state to an expanded state when inserting said strengthening portion in the heart lumen. In a further embodiment, the one or more positioning members may each comprise a hook shape to further improve fixation of the position and orientation of the heart support device within the heart lumen.

During circulatory assistance, the dynamic volume body may be inflated and deflated in a cyclical manner through the supply and retrieval of a gas or a fluid. For that purpose an embodiment is provided wherein the internal member is attached to a catheter, e.g. in the form of a tubular catheter having a passageway extending there through. The catheter allows supply and retrieval of gas or fluid to or from the internal member and the dynamic member. The catheter may also be convenient during placement of the heart support device within the heart lumen, where the heart support device is brought from a collapsed state to an expanded state by supplying gas or fluid through the catheter into the wall strengthening portion.

In an advantageous embodiment, the catheter is connected to the one or more positioning members, wherein the one or more positioning members are e.g. tubular positioning members connected to the dynamic volume body. In this embodiment the one or more positioning members not only provide fixation of the heart support device within the heart lumen but also allow the supply and retrieval of a gas or fluid to or from the internal member and dynamic member thereof.

This embodiment thus provides an efficient arrangement wherein the one or more positioning members not only provide structural and positional support to the heart support device but also enable cyclical inflation and deflation of the dynamic member to provide circulatory assistance.

According to inventive embodiments, the external shell element and/or the wall strengthening portion may each comprises a circumferential overlap region. Each circumferential overlap region is configured for engagement with a healthy wall part surrounding a weakened wall or ischemic area of the heart, typically an aneurysm, so that sufficient and reliable support can be provided for preventing inward or outward protrusion of the weakened wall or ischemic area during pressure gradients.

In a further embodiment, the heart support device may further comprise a first tubular member connecting the external shell element and the wall strengthening portion, the first tubular member being in communication with the dynamic member. This embodiment is particularly advantageous for inflating the dynamic member from outside of the heart.

In a further advantageous embodiment, the wall strengthening portion comprises an inflatable wall strengthening chamber configured for expanding the wall strengthening portion into a static inflated state in the heart lumen. This embodiment allows the wall strengthening portion to be expanded through inflation, wherein the base chamber of the wall strengthening portion may be inflatable with a liquid medium, a gel, or even a powder, all of which provide a substantially stiff form to the wall strengthening portion when it is inflated.

According to the invention, the dynamic member may comprise a stretchable membrane forming a balloon chamber. The stretchable membrane is able to provide the dynamic member with a varying volume as is stretches and shrinks in cadence with a detected heart rate.

In an embodiment, the stretchable membrane is hermetically attached to the wall strengthening portion along a circumferential portion thereof, the stretchable membrane and the wall strengthening portion forming the balloon chamber. In this embodiment the stretchable membrane may be envisaged as a dome-like member attached to the wall strengthening portion. This allows the wall strengthening portion to have a different geometry and be made of different material, wherein the wall strengthening portion may exhibit a different level of compliance, elasticity, and/or deformability than the stretchable membrane.

In an alternative embodiment, the stretchable membrane is a substantially spherical membrane in an inflated state. In contrast to the previous embodiment, in this embodiment the stretchable membrane may be envisaged as a separate spherical balloon, wherein the spherical membrane is in communication with e.g. a pumping device for changing its diameter so as to displace a required amount of blood volume through the heart lumen.

In an embodiment the stretchable membrane may comprise an elastic cloth for good fibrin encapsulation and to minimize thrombogenicity of the membrane. In some embodiments the stretchable membrane may even comprise a titanium netting for improving the durability of the dynamic member.

To provide good support to the heart wall as well as retaining as much of the original geometry of the heart as possible, in particular a weakened wall thereof, the external shell element may comprises a substantially non-resilient bowl-shaped geometry. The bowl-shaped geometry is adapted to receive the weakened wall of the heart and to provide a regular and natural shape of the weakened wall. In some embodiments the external shell element may comprise a bowl-shaped geometry that is specifically tailored to a certain natural shape of the heart wall of a patient.

In a typical and practical embodiment, the heart support device of the present invention may comprise a pumping device in communication with the internal member, in particular the dynamic member thereof. The pumping device may be controlled through a control unit which is adapted to analyse electrical activity of the heart for determining a heart pumping rate to be followed by the heart support device. In certain situations the heart support device may even be used in conjunction with a pacemaker when required, wherein the heart support device provides circulatory assistance in cadence with the pacemaker, thus wherein electrical activity of the pacemaker imposes the frequency of inflation and deflation of the internal member for synchronous assistance. Also use in conjunction with an implantable cardioverter defibrillator (ICD) is possible.

SHORT DESCRIPTION OF DRAWINGS

The present invention will be described more fully hereinafter based on a number of exemplary embodiments with reference to the drawings, wherein.

DETAILED DESCRIPTION OF EXEMPLARY EMBODIMENTS

Figure 1:
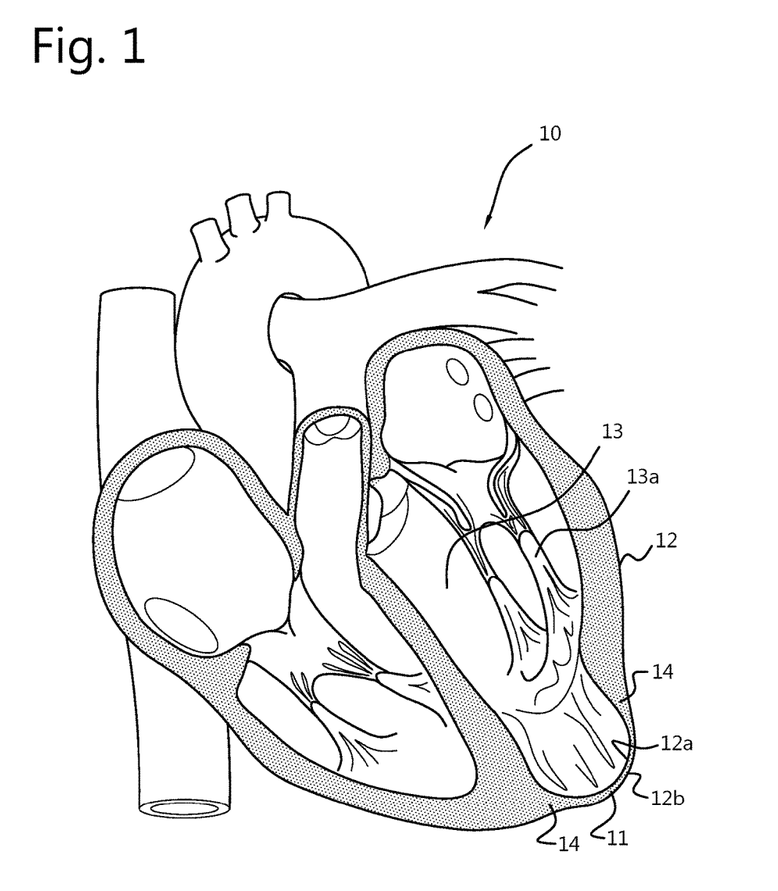
FIG. 1 shows an exemplary embodiment of a heart having weakened myocardial tissue or an ischemic area.

FIG. 1 shows an exemplary embodiment of a heart suffering from an aneurysm according to the present invention. In the exemplary embodiment shown, the heart 10 comprises a weakened wall 11 (e.g. an ischemic area or cardiac aneurysm) in the heart wall 12 of a heart lumen 13. The aneurysm 11 forms a weakened part of the heart wall 12 and is often caused by a myocardial infarction due to a coronary blockage, also known as a "heart attack". Blocked coronary blood flow typically leads to a lack of oxygen to be supplied to parts of the heart wall 12, so that affected myocardial tissue dies. This causes less mechanical function of the heart, which itself leads to cardiogenic shock. Dead myocardial tissue does not grow back and is mostly replaced by collagen scar tissue (fibrin).

In light of the present invention, the terms such as "weakened wall", "ischemic area" and "aneurysm" can be used interchangeably, even though they may have different medical meaning. For further ease of reference, the term "weakened wall" will be used to generally indicate a weakened part 11 of the heart wall 12 that is typically caused (however, not necessarily) by an ischemic area 11 and/or post ischemic area such as an (pseudo) aneurysm 11.

The weakened wall 11 in the heart wall 12 is often more compliant and elastic than healthy surrounding wall tissue 14. In case of a left ventricular aneurysm, for example, the compliance of the aneurysm 11 may cause excessive outward and inward protrusion, bulging or "ballooning" of the aneurysm 11 during systolic and diastolic phases inside the heart lumen 13, e.g. the left ventricle lumen. The ballooning may increase due to the increase in wall tension, according to La Pace law. This device seeks to lower the direct pressure on the affected area and therefore stop or even reverse the growth of the ventricular aneurysm.

In the acute setting a known complication after a transmural infarction is a ventricular wall rupture, this device seeks to reduce the direct pressure on the affected area and therefore to lower the risk of the life threatening complication.

In addition to the weakened wall 11 being more compliant and less elastic than surrounding healthy wall tissue 14, the weakened wall 11 does not have the ability to contract as muscle tissue in the affected area is non-functional. In case of a left ventricular aneurysm, for example, the heart wall 12 is partially compromised and its inability to sufficiently contract generally leads to heart failure.

Currently there is no successful minimal invasive therapy which reduces mortality rates associated with an aneurysm 11 of heart and which is capable of providing quality of life for impaired patients suffering from such an aneurysm 11. Roughly 85% of all aneurysms of heart lie in the anterior lateral plane, near the apex, and nearly all such aneurysms are post ischemic aneurysms.

In view of the above there is a need for improved survival rates and quality of life of patients suffering from a myocardial ischemic area 11 as described above, e.g. an aneurysm 11, wherein rupture of the ischemic area 11 is prevented and, at the same time, circulatory assistance is provided for compensating a certain level of heart failure, which is dependent on de severity of the infarction.

According to the present invention a heart support device is provided fulfilling this need. The heart support device provides both continuous structural support to the affected weakened wall 11, such as an aneurysm 11, preventing inward and outward ballooning thereof during systolic and diastolic phases, as well as providing circulatory assistance for compensating a level of heart failure.

Figure 2:
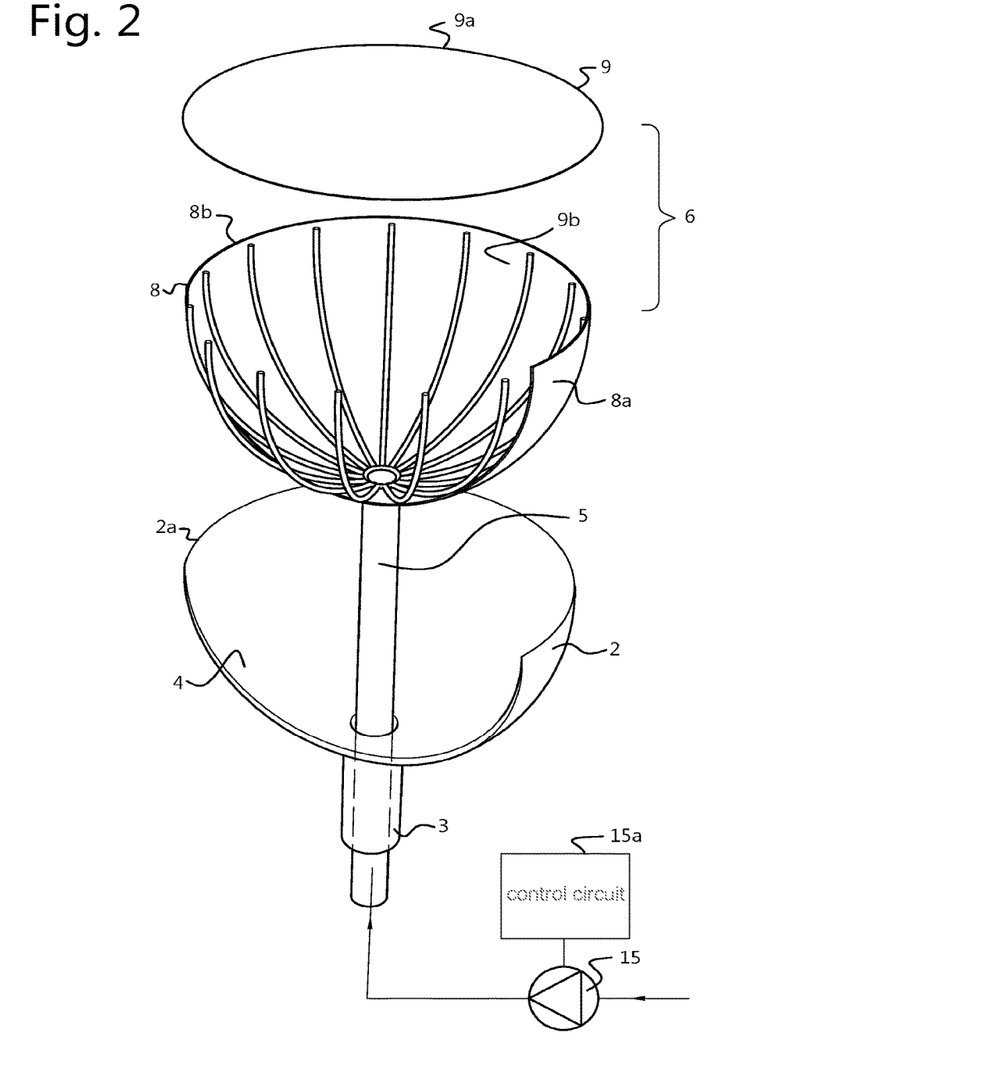
FIG. 2 shows an exploded view of an embodiment of a heart support device according to the present invention.

FIG. 2 shows an exploded view of an embodiment of a heart support device according to the present invention. In the embodiment shown, the heart support device 1 comprises an internal member 6 to be disposed inside a heart lumen 13 and having a dynamic volume body. The internal member 6 is provided with a substantially stiff wall strengthening portion 8 arranged to engage an inner wall surface of the heart 10 in operation and where a dynamic member 9 is provided that is inflatable to assist pumping action in the heart 10, thereby providing circulatory assistance.

In the embodiment shown in FIG. 2 the heart support device 1 further comprises an external shell element 2 having a support surface 4 of a (substantially) rigid material. The external shell element 2 is arranged to engage an outer wall surface 12b of the heart wall 12, (e.g. the aneurysm 11), preventing excessive protrusion thereof during systolic or diastolic pressure levels inside the heart lumen 13. Further, the external shell element 2 also imposes a correct shape of the outer wall surface 12b close to an original shape of the heart wall 12 prior to the development of the ischemic area 11. To that end, the external shell element 2 may comprises a substantially non-resilient bowl-shaped geometry.

The internal member 6 is arranged to provide support to the inner wall surface 12b (i.e. a weakened part of the wall) during e.g. systolic and/or diastolic pressure levels in the heart lumen 13 and to prevent excessive inward protrusion and a subsequent decrease of ejection fraction.

The heart support device 1 of the present invention embodiments having the external shell element 2 (e.g. shown in FIG. 2) provides both two-sided support of a weakened wall 11 as well as circulatory assistance of the heart 11 by means of the internal member 6 which is to be disposed in the heart lumen 13. In operation, the weakened wall 11 is effectively clamped between the external shell element 2 and the wall strengthening portion 8 and supported thereby at the inner and outer wall surfaces 12a, 12b during systolic and diastolic pressure levels in the heart lumen 13. The inflatable dynamic member 9 is designed to inflate and deflate in synchronicity with a detected heart rate for compensating a level of heart failure as a result of ischemia (cardiogenic shock) or the aneurysm 11. When the dynamic member 9 inflates the effective volume of the heart lumen 13 decreases and a volume of blood is displaced. For a left ventricular aneurysm this implies that the inner member 6 is disposed in the left ventricle and the dynamic member 9 assists the ejection of blood through the aortic valve. In most embodiments, the dynamic member 9 is connected to a pumping device 15 comprising a control circuit 15a monitoring a patient's heart rate and determining required volumetric changes of the dynamic member 9 over time in response to the detected heart rate. The pumping device 15 may supply and retrieve a gas or a fluid to or from the dynamic member 9 through an external tubular member 3 which is in communication with the dynamic member 9 and the pumping device 9. The pumping device 15 may be arranged to inflate during the systole phase and deflate during the diastole phase, e.g. using proper sensing and synchronization components.

It is important to note that during operation, the internal member 6 is configured and positioned for not interfering with papillary muscles 13a inside the heart lumen 13, so that valve leakage is avoided.

In an embodiment, the wall strengthening portion 8 is expandable from a collapsed state to an expanded state. The collapsed state allows for delivery of the internal member 6 into the heart lumen 13 through a small hole in the heart wall 12, for example, through the affected area 11, or through a catheter 40 (see embodiments described below with reference to FIG. 9-11b). Once the internal member 6 is in the right position in the heart lumen 13, the wall strengthening portion 8 may be brought into the expanded state for snug engagement with the inner wall surface 12a of the affected area 11. In advantageous embodiments, the wall strengthening portion 8 may comprise an expandable netting, such as a expandable titanium netting, which is able to act as an unfolding umbrella once delivered in the heart lumen 13.

In an embodiment, the external shell element 2 comprises a circumferential overlap region 2a. The circumferential overlap region 2a is configured for engagement of the external shell element 2 with a healthy wall part 14 surrounding the weakened wall 11, so that sufficient and reliable support can be provided for preventing inward or outward protrusion or ballooning of the ischemic area 11 during pressure gradients over the heart wall 12 and the ischemic area 11. Likewise, in an embodiment the wall strengthening portion 8 may comprise a circumferential overlap region 8a, wherein the wall strengthening portion 8 is in snug engagement with the healthy wall part 14 in vivo for supporting the ischemic area/aneurysm 11 during pressure gradients over the heart wall 12. Maximum pressure gradients typically occur during systolic and diastolic motion of the heart 10, wherein systolic pressure typically causes an aneurysm 11 or an ischemic area 11 to protrude or balloon outward whereas diastolic pressure typically leads to inward protrusion or ballooning of the aneurysm 11 or the ischemic area 11.

In an embodiment, the heart support device 1 may further comprise a first tubular member 5 connecting the external shell element 2 and the wall strengthening portion 8, wherein the first tubular member 5 is in communication with the dynamic member 9. In most embodiments the first tubular member 5 extends through a small hole in the heart wall 12, typically through the affected area 11 itself. The first tubular member 5 may often comprise a passageway through which a fluid can be supplied or retrieved for inflating or deflating the dynamic member 9. The first tubular member 5 may further comprise a suitable length for clamping the aneurysm 11 between the wall strengthening portion 8 and the external shell 2, which length may depend on the particular size and thickness of the ischemic area/aneurysm 11 at issue. Clamping the ventricular wall 12 between the wall strengthening portion 8 and the external shell element 2 provides support against excessive bulging and ballooning of the ischemic area 11. As the first tubular member 5 extends through the heart wall 12, e.g. through the aneurysm 11, sideways sliding movement of the heart support device 1 along the heart wall 12 is also further avoided, thus keeping the heart support device 1 firmly in place around the aneurysm 11.

According to the invention, the dynamic member 9 may comprise a stretchable membrane 9a forming a balloon chamber 9b. The membrane 9a allows for volumetric changes of the balloon chamber 9b in relation to the required volume of blood to be displaced. In advantageous embodiments the stretchable membrane 9a comprises an elastic cloth, which facilitates fibrin encapsulation thereof such that the propensity to blood clot formation, i.e. thrombosis, on the stretchable membrane 9a is minimized. The stretchable membrane 9a may also comprise a titanium netting, which further improves anti-clotting characteristics, by promoting ingrowth of cells, as well as the durability of the membrane 9a.

In the exploded view shown, the stretchable membrane 9a may be hermetically attached to the wall strengthening portion 8 along a circumferential portion 8b thereof, wherein the stretchable membrane 9a and the wall strengthening portion 8 form the balloon chamber 9b. This embodiment may provide a collapsible internal member 6, as the wall strengthening portion 8 may comprise e.g. a collapsible titanium netting and the stretchable membrane 9a may be foldable.

Figure 3:
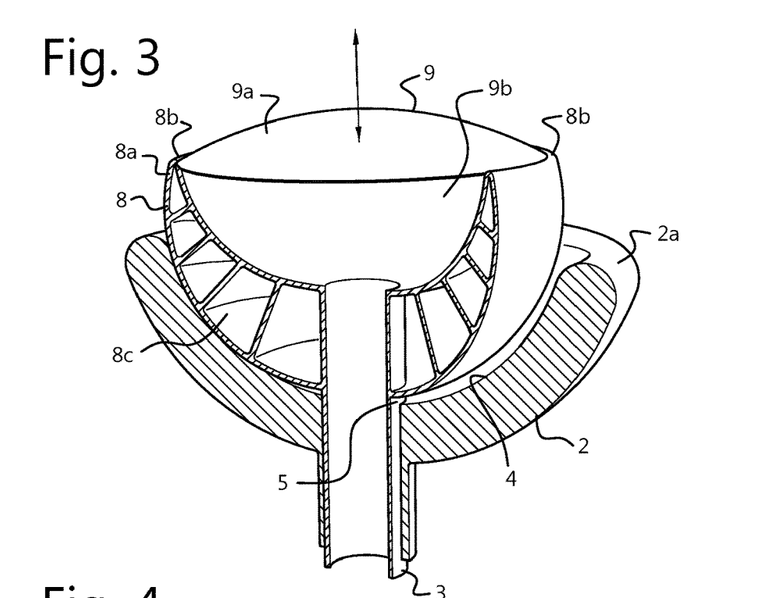
FIG. 3 shows a cross sectional view of an embodiment of a heart support device according to the present invention.

FIG. 3 shows a cross sectional view of an embodiment of a heart support device 1 according to the present invention. In this embodiment, the wall strengthening portion 8 may comprise an inflatable base chamber 8c configured for expanding the wall strengthening portion 8 into a static inflated state in the heart lumen 13. The wall strengthening portion 8 may be envisaged as a collapsible elastic pouch comprising multiple base chambers 8c.

The wall strengthening portion 8 may be expandable and may be unfolded or inflated with a liquid medium, a gel comprising e.g. silicone, a powder or a gas. When using a powder, the powder may be kept in e.g. a membrane and when placed in vacuum it keeps a solid form. When the wall strengthening portion 8 is in the collapsed state and delivered into the heart lumen 13, the fluid, gel or powder may be provided through the first tubular member 5 for injecting the fluid, gel or powder into the base chambers 8c. Injecting the fluid, gel or powder into the base chamber 8c inflates the wall strengthening portion 8 until snug engagement of the wall strengthening portion 8 with the inner wall surface 12a is reached. In most embodiments the wall strengthening portion 8 engages a left ventricular inner wall surface 12a in vivo.

The wall strengthening portion 8 readily conforms to the inner wall surface 12a for optimal support of the ischemic area/aneurysm 11. In the static inflated state, the wall strengthening portion 8 remains sufficiently stiff for withstanding pressure gradients during e.g. the systolic or diastolic phase, so that the ischemic area or aneurysm 11 is prevented from ballooning and possible rupture as a result thereof. Of course, in some embodiments the wall strengthening portion 8 may also be self-expandable and may comprise an elastic or sponge like body that is compressible and which attains a desired expanded shape once fully expanded in the heart lumen 13.

In the embodiment shown, the stretchable membrane 9a is hermetically attached to the wall strengthening portion 8 along a circumferential portion 8b thereof, wherein the stretchable membrane 9a and the wall strengthening portion 8 form the balloon chamber 9b. In advantageous embodiments, the stretchable membrane 9a may be integrally formed with the wall strengthening portion 8 and as such may be of the same material, thereby providing a smooth and seamless outer surface to the internal member 6 that is less susceptible to tearing and leakage. The balloon chamber 9b is in communication with the pumping device 15 through the first tubular member 5 and external tubular member 3. The first and external tubular member 5, 3 thus comprise a passageway for inflating the base chambers 8c as well as a passageway for inflating the balloon chamber 9b.

Figure 4:
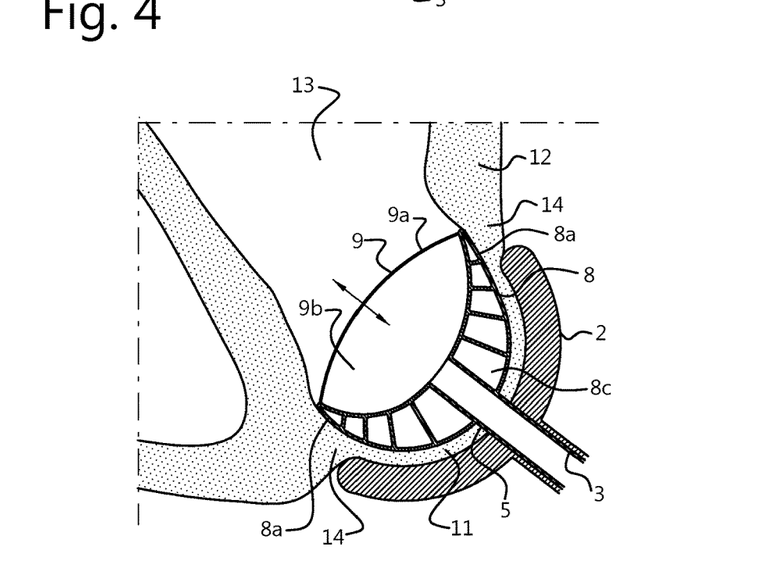
FIG. 4 shows a heart support device in vivo according to a present invention embodiment.

FIG. 4 shows a heart support device in vivo according to a present invention embodiment. In this particular embodiment the wall strengthening portion 8 and external shell element 2 engage the internal and external wall surfaces 12a, 12b respectively, wherein the circumferential overlap region 8a of the wall strengthening portion 8 and the circumferential overlap region 2a of the external shell element 2 each engage a healthy wall part 14 of the heart wall 12 surrounding the aneurysm 11. The circumferential overlap regions 2a, 8a provide support to the external shell element 2 and the wall strengthening portion 8 during e.g. systolic and diastolic phases, wherein the healthy wall part 14 is less resilient or compliant and considerably more stable. Pressure applied across the wall strengthening portion 8 and the external shell element 2 is therefore transferred and distributed along the circumferential overlap regions 2a, 8a, thereby relieving pressure forces on the weakened wall, ischemic area or aneurysm 11.

Figure 5:
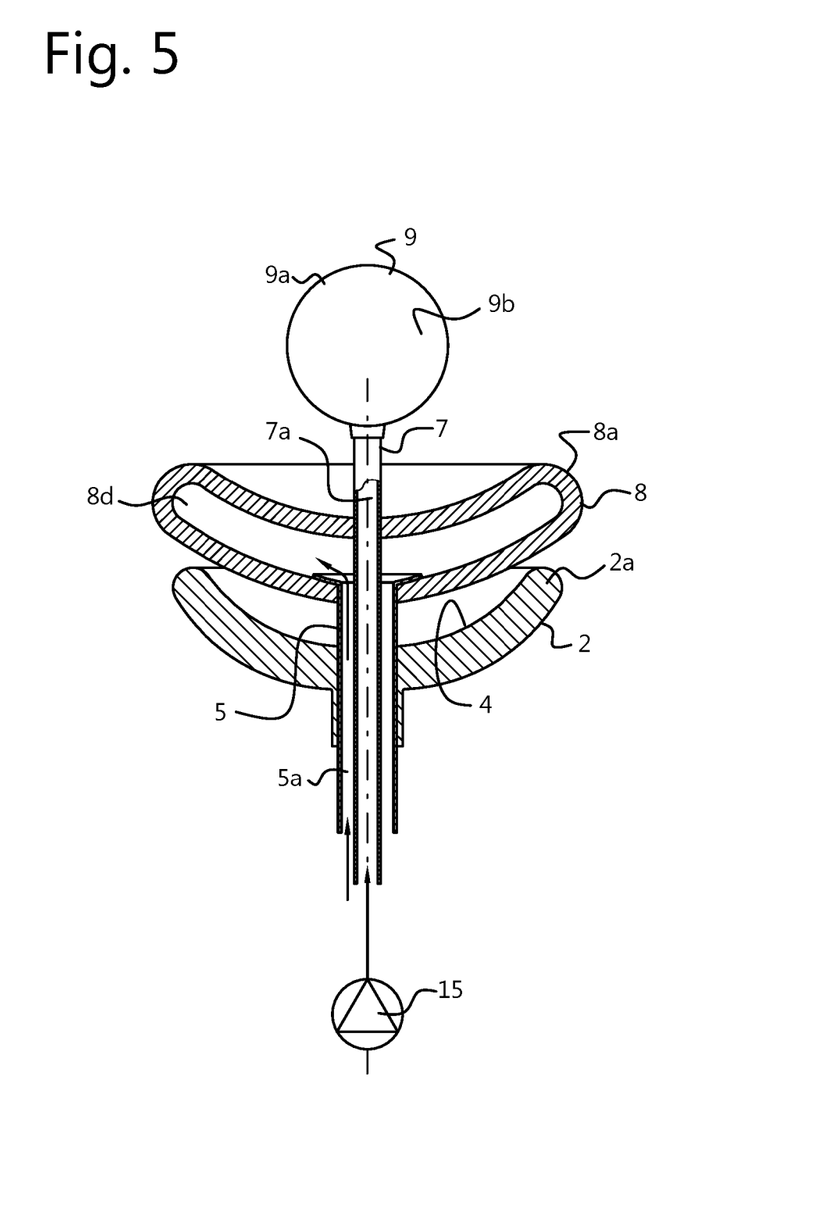
FIG. 5 shows cross sectional view of a heart support device according to another present invention embodiment.

FIG. 5 shows cross sectional view of a heart support device according to another present invention embodiment. In this particular embodiment the internal member 6 comprises a dynamic member 9 having a stretchable membrane 9a, but in this depicted embodiment the stretchable membrane 9a is a substantially spherical membrane in an inflated state enclosing the balloon chamber 9b. The spherical membrane 9a is in communication with the pumping device 15 and changes in diameter for displacing a required amount of blood volume. The dynamic member 9 is connected to the wall strengthening portion 8 through a second tubular member 7 interposed there between. The second tubular member 7 comprises a passageway 7a for supplying or retrieving a gas to inflate or deflate the dynamic member 9.

As with the embodiment shown in FIG. 3, the wall strengthening portion 8 may also comprise an inflatable base chamber 8d configured for expanding the wall strengthening portion 8 into a static inflated state in the heart lumen 13. Once inflated with e.g. a suitable fluid or gel such as a silicone based fluid or gel, the wall strengthening portion 8 engages the inner wall surface 12a and provides a substantially stiff support to the affected area 11. In most embodiments a passageway 5a is provided for supplying the suitable fluid or gel to the base chamber 8b. In this embodiment the wall strengthening portion 8 may be viewed as a stretchable, foldable, and/or elastic pouch that can be delivered into the heart lumen 13 in a collapsed state and inflated into a static inflated state once correctly delivered inside heart lumen 13.

Figure 6:
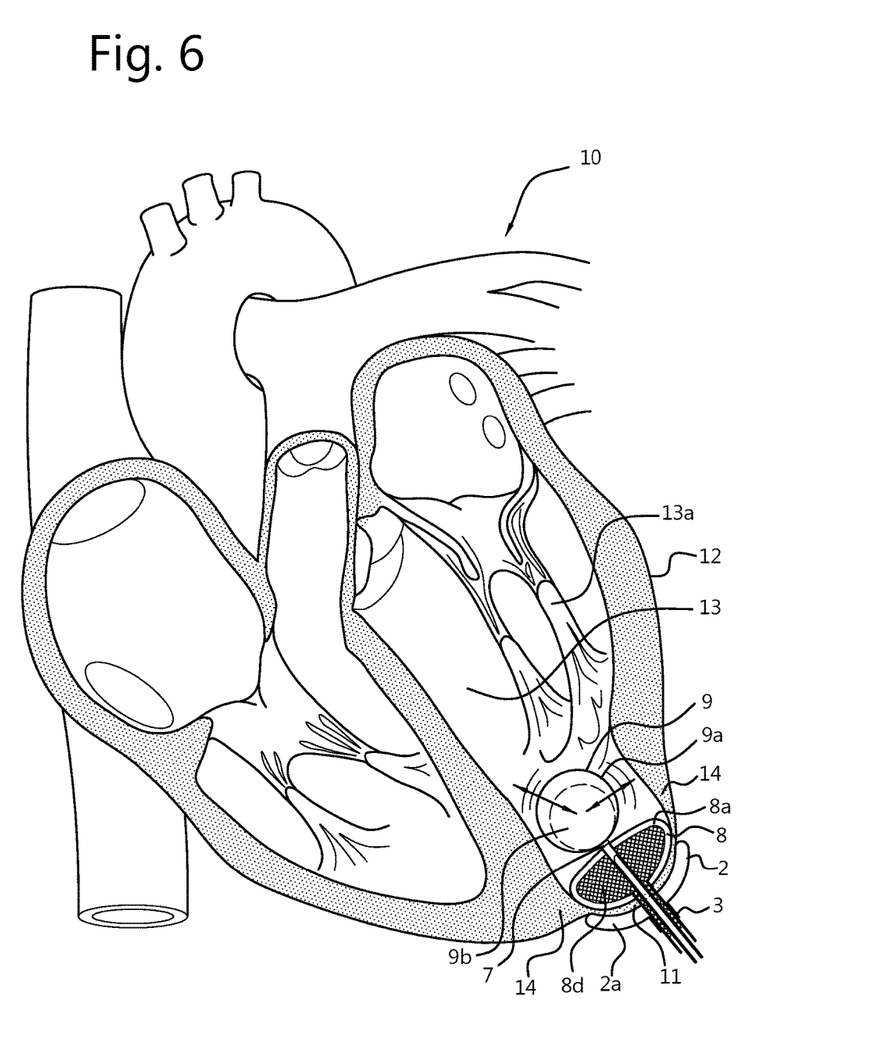
FIG. 6 shows a heart support device in vivo according to another present invention embodiment.

FIG. 6 shows a heart support device in vivo according to another present invention embodiment. The depicted embodiment of the heart support device 1 resembles the embodiment of FIG. 5, wherein the internal member 6 comprises a separate wall strengthening portion 8 and dynamic member 9 that are interconnected by a second tubular member 7 interposed there between. According to the invention, the internal member 6, in particular the dynamic member 9, is configured for not interfering with papillary muscles 13a in the heart lumen 13, e.g. the left ventricle lumen. As with all other embodiments, the wall strengthening portion 8 may be expandable and may comprise an inflatable pouch having a base chamber 8d, which can be filled with a suitable material such as a pressurized gas, a fluid, a gel or a powder to bring the wall strengthening portion 8 into a static inflated state for snug engagement with an inner wall surface 12a. The external tubular member 3 is connected to the first tubular member 5, which in turn is connected to the second tubular member. Each tubular member comprises a passageway for supplying or retrieving a fluid to inflate or deflate the dynamic member 9. In certain embodiments the external and first tubular members 3, 5 comprise an additional passageway for supplying a fluid, a gel or powder to the base chamber 8b if the wall strengthening portion 8 comprises such a inflatable chamber 8d.

According to the invention, the heart support device 1 is adapted to provide circulatory assistance for various degrees of heart failure following e.g. a myocardial infarction, and at the same time provide structural support to the affected area 11 for preventing excessive ballooning thereof during systolic and diastolic phases. To that end the heart support device 1 may typically comprise a pumping device 15 which is in communication with the internal member 6, in particular the dynamic member 9, for inflation and deflation thereof in synchronicity with a detected cardiac cycle.

In many embodiments the pumping device 15 may further comprise a control unit 15a adapted to analyse electrical activity of the heart 10 for determining a heart pumping rate to be followed by the heart support device 1. The heart support device 1 of the present invention may even be connected to a pacemaker, wherein electrical activity of the pacemaker imposes the frequency of inflation and deflation of the internal member 6 for synchronous circulatory assistance. The heart support device 1 of the present invention is very well suited for treating patients with e.g. a left ventricular aneurysm, wherein the internal member 6 is disposed in the left ventricular lumen of the heart 10 and the internal member 6 displaces a required volume of blood from the left ventricle into the aorta.

The heart support device 1 of the present invention has many advantages with regard to implant delivery techniques. Since the internal member 6 may be collapsible and expandable, in particular the wall strengthening portion 8, the heart support device 1 may be delivered using a probe that keeps the heart support device 1 in a collapsed state while being moved through e.g. an artery toward a delivery site, such as a left ventricle. It is even conceivable that the heart support device 1 may be adapted for percutaneous delivery, wherein a delivery probe holding a collapsed heart support device 1 is used to puncture through the skin, then through the affected heart wall 12 comprising the aneurysm 11, and subsequently into the heart lumen 13. By retracting the probe the internal member 6 is able to expand into the expanded state for snug engagement with the inner heart wall 12a. Percutaneous delivery may require that the external shell element 2 is expandable as well from a collapsed state to an expended state. To that end the external shell element 2 may comprise an expandable umbrella-like netting (e.g. titanium netting) or may comprise an inflatable pouch or sponge-like body having an inflatable shell chamber that can be inflated with a suitable fluid or gel (e.g. silicone) toward a static expanded state. In this way the entire heart support device 1 is expandable and suitable for percutaneous delivery.

Figure 7:
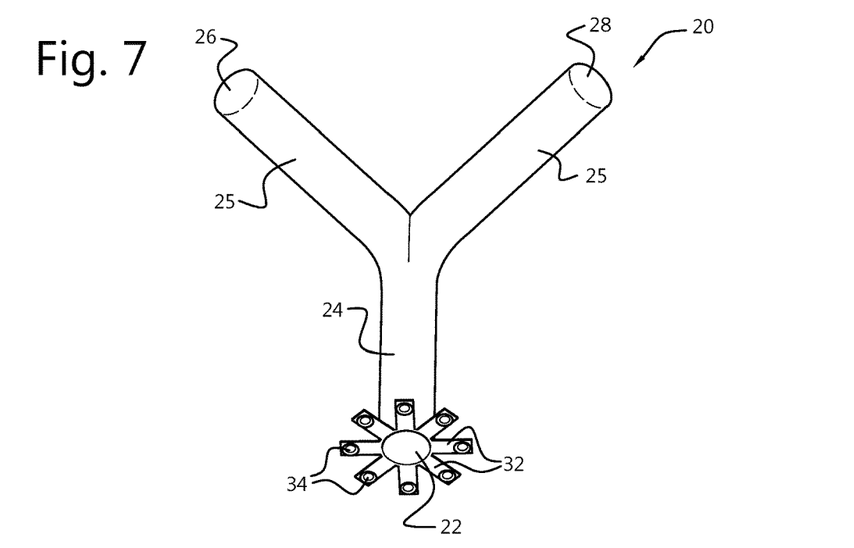
FIG. 7 shows an embodiment of a delivery device according to the present invention.
Figure 8:
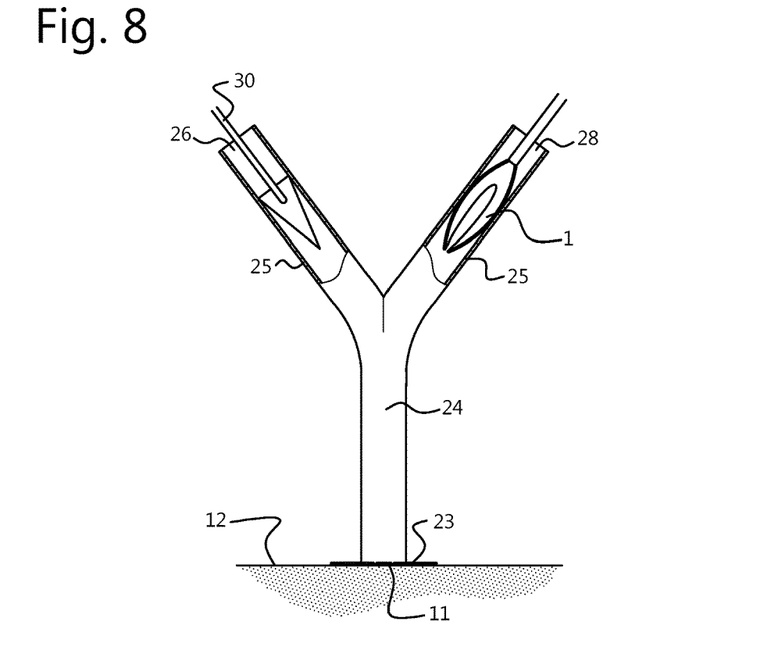
FIG. 8 shows another embodiment of a delivery device according to a present invention embodiment.

FIG. 7 and FIG. 8 each show an embodiment of a delivery device according to the present invention, wherein the delivery device 20 is arranged for delivering the heart support device 1 of the present invention in a collapsed state into a heart lumen 13. In the embodiment shown, the delivery device 20 comprises a central conduit 22 attachable to a surface of the heart wall 12 at a distal end 24 and further comprises a first conduit 26 and a second conduit 28 attached to the central conduit 22 at a proximal end 25. In a typical embodiment, the first and second conduits 26, 28 are disposed at an angle yielding a Y-shaped delivery device 20 as depicted. The first conduit 26 may be adapted for allowing access of a surgical instrument 30 to the heart wall 12, in particular the aneurysm 11, for making a hole there through. The second conduit 28 may be adapted to guide a collapsed heart support device 1 through the hole in the heart wall 12. Hence, first the surgical instrument 30 may be inserted into the first conduit 26 and retrieved once the hole in the heart wall 12 is completed, then the collapsed heart support device 1 may be inserted into the second conduit 28 and delivered through the hole into the heart lumen 13.

In advantageous embodiments the distal end 24 of the delivery device 20 may comprise a wall connecting member 32 provided with a plurality of suction cups 34 adapted for temporarily affixing the delivery device 20 to the heart wall 12. The plurality of suction cups 34 allow for a benign engagement of the delivery device 20 with the heart wall 12, i.e. the aneurysm 11, without damaging wall tissue.

Figure 9:
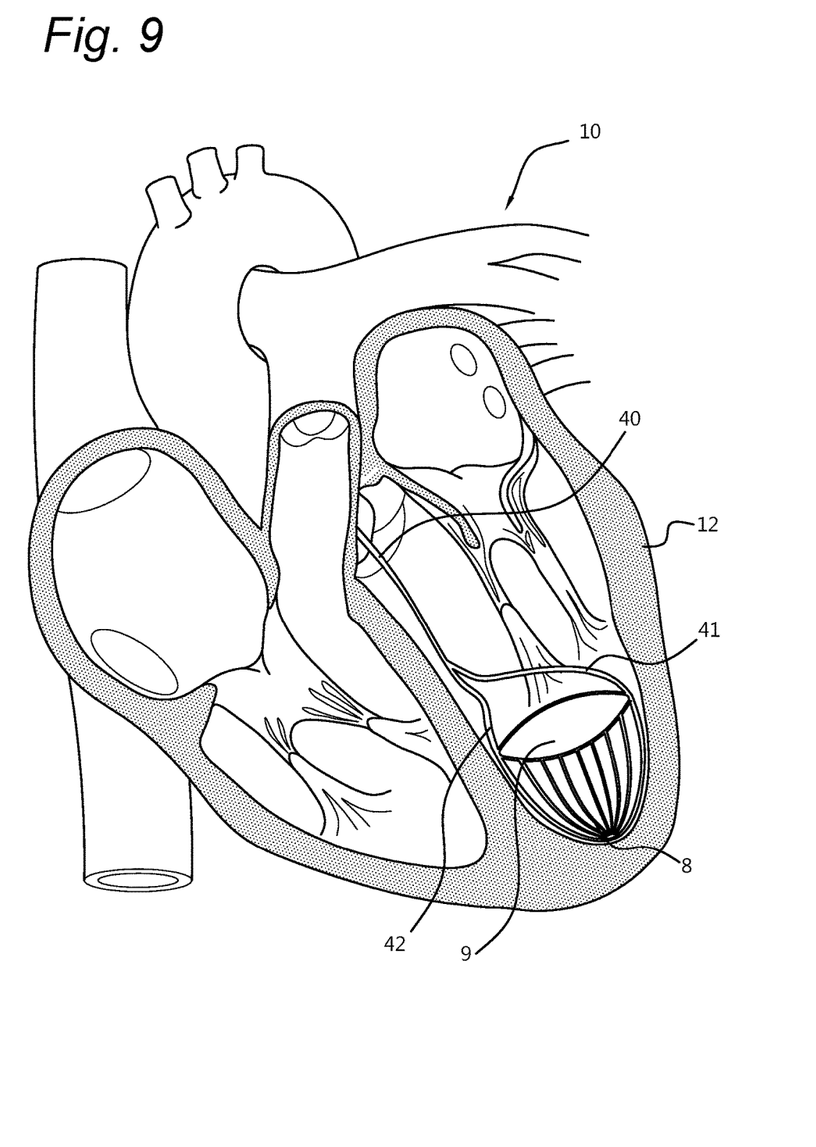
FIG. 9 shows a further embodiment of a present invention heart support device positioned inside a heart.

FIG. 9 shows an embodiment of a heart support device arranged in a heart lumen (left ventricle) according to the present invention. In the embodiment shown, the heart support device may comprise a wall strengthening portion 8 that is expandable, so as to engage the heart wall 12 of the heart 10, in particular an inner wall surface thereof (in this case the lower part of the left ventricle). The snug engagement of the wall strengthening portion 8 allows blood pressure changes to be mostly absorbed by the wall strengthening portion 8, so that the heart wall 12 experiences a reduced blood pressure and further weakening or even rupture of the heart wall 12 is avoided.

The inflatable dynamic member 9 may comprises a membrane 9a (like in the embodiments described above) which e.g. constantly changes between a convex and concave shape during circularity assistance. The membrane 9a may be arranged such that the resulting pressure wave is directed towards the associated heart valve to ensure that blood can be ejected efficiently there through.

In an embodiment, the wall strengthening portion 8 is expandable and may be arranged for expansion by umbrella like stays or tensioning lines (which may be operated through a catheter member 40, see further below). This embodiment allows easier positioning and deployment of the heart support device in the heart lumen 13.

For improved support of the heart wall 12, the wall strengthening portion 8 comprises an inflatable cup shaped body in a further embodiment, allowing for conformal engagement with the inner surface of the heart wall 12. The cup shaped body of the wall strengthening member 8 e.g. tightly fits in an apex portion of the heart lumen 13, e.g. near the apex of a left ventricular lumen, thereby providing good support in case of a weakened heart wall or aneurysm as described above.

Further to the embodiment shown, the internal member 6 comprising the wall strengthening member 8 and inflatable dynamic member 9 may comprise one or more positioning members 41, 42. The positioning members 41, 42 ensure the heart support device remains firmly in place and affixed in a desired orientation within the heart lumen 13 in operation, so that optimum circulatory assistance is maintained during cardiac cycle. The one of more positioning member 41, 42 are further adapted and positioned to prevent interference with internal heart structures such as papillary muscles and/or chordae tendineae, e.g. as shown in the embodiment of FIG. 9, where the positioning members 41, 42 form an arc above the inflatable dynamic member 9.

In an advantageous embodiment, the one or more positioning members 41,42 are congruent to an inner surface of the heart lumen 13 to improve fixation of the heart support device when in use yet keeping contact forces on the inner surface to a minimum. In an exemplary embodiment the one or more positioning members 41, 42 comprise an arc shape whereby a curvature or internal surface of the heart lumen 13 can be followed or matched. The one or more arc shaped positioning members 41, 42 allow fixation forces to be distributed along the curvature or inner surface of the heart lumen 13, resulting in an improved fixation of the heart support device.

Figure 10:
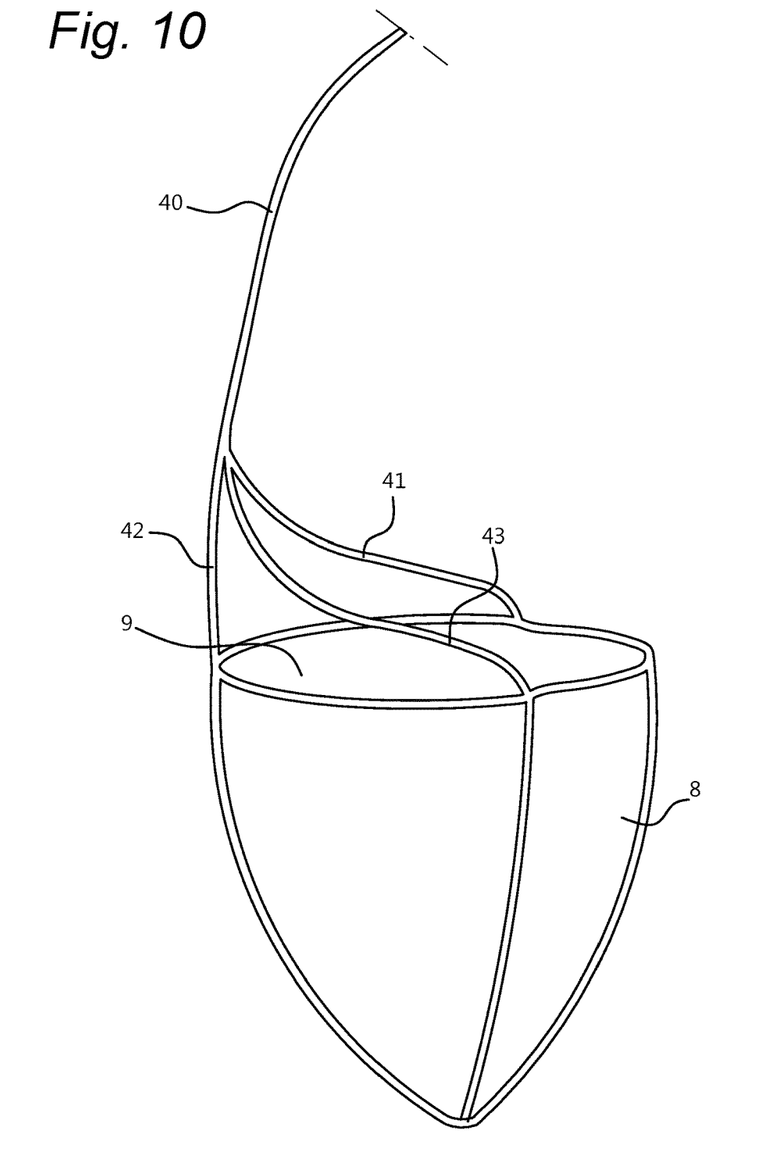
FIG. 10 shows a side view of a further embodiment of a heart support device according to the present invention.

FIG. 10 shows a further embodiment of the one or more positioning members as used in the present invention. In the embodiment shown, the one or more positioning members 41, 42, 43 are provided with an arc shape for congruent engagement with a curvature or part of an internal surface of the heart lumen 13, thereby firmly affixing the position and orientation of the heart support device within the heart 10 for optimum functioning. The one or more positioning members 41, 42, 43 may in an alternative embodiment be provided with small extensions (e.g. shaped as pins, hooks, etc.) to anchor the heart support device in the lumen 13.

In an advantageous embodiment the one or more positioning members 41, 42, 43 are tubular positioning members arranged for inflating and deflating the dynamic member 9 to provide circulatory assistance. In a further advantageous embodiment, the one or more positioning members 41, 42, 43 are tubular positioning members arranged for inflating and deflating the wall strengthening portion 8 from e.g. a collapsed state to an inflated state, which is very useful when positioning the heart support device in the heart lumen 13 through a catheter 40 for example.

As with other embodiments described herein, the dynamic member 9 may comprise an inflatable, stretchable membrane 9a forming a balloon chamber. The membrane 9a allows for volumetric changes of the balloon chamber in relation to the required volume of blood to be displaced. The stretchable membrane 9a allows efficient ejection of blood out of the heart lumen. The material and dimensions of the stretchable membrane 9a may be selected to obtain a suitable operation and life time of the heart support device of the present invention embodiments. E.g. the thickness may vary over the surface of the membrane 9a, in order to provide a predetermined expansion profile of the dynamic member 9. The material may be selected to have a first elasticity modulus up to a predetermined expansion percentage, and a second, lower, elasticity modulus above that predetermined expansion percentage.

As shown in the FIG. 10 embodiment, the one or more positioning members 41, 42, 43 may extend along the wall strengthening member 8 providing further structural stiffness thereto.

In an advantageous embodiment, the internal member 6 is attached to a catheter 40, e.g. a tubular catheter member 40, allowing the dynamic member 9 to be operated via the catheter 40. The embodiment with a catheter 40 also allows the heart support device to be positioned via the arteries or vessels in communication with the heart, which makes a complex and risky heart surgery placement unnecessary.

Advantageously, the catheter 40 may be connected to the one or more positioning members 41, 42, 43 which in turn are in communication with the dynamic volume body of the internal member 6 (more specifically dynamic member 9), as well as (in some embodiment) the expandable/inflatable wall strengthening portion 8. Thus, catheter member 40 may be used to both allow expansion of the wall strengthening portion 8 during placement of the heart support device in the heart as well as cyclical inflation and deflation of the dynamic member 9 during circulatory assistance.

Figures 11A, 11B:
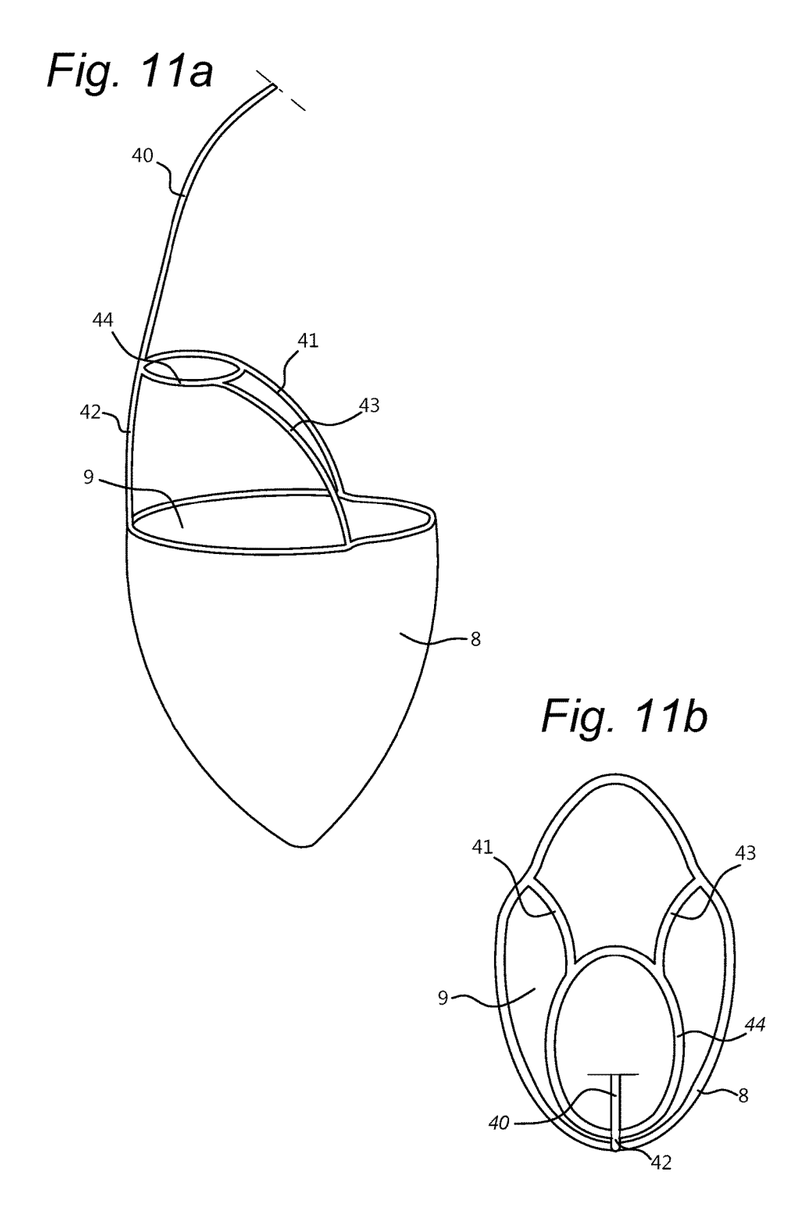
FIGS. 11a and 11b show a side view and top view, respectively, of an alternative embodiment of the heart support device of FIG. 10.

FIGS. 11a and 11b show a side view and top view, respectively, of an alternative embodiment of the heart support device of FIG. 10. In the embodiment shown, the one or more positioning members 41, 42, 43 may further comprise a ring shaped member 44, which further facilitates fixation of the heart support device within the heart lumen 13 of the heart, without obstructing or hampering any further internal heart components.

In an advantageous embodiment, the ring shaped member 44 comprises a flexible tubular part connected to the catheter member 40 and the one or more positioning members 41, 42, 43. That is, one or more positioning members 41, 42, 43 may be connected to the catheter member 40 through the heart valve engagement member 44. Inflation and deflation of the dynamic member 9 is therefore achieved by supplying and retrieving a fluid through the catheter member 40, the heart valve engagement member 44 and one or more positioning members 41, 42, 43.

In connection with these embodiments, the catheter 40 and the one or more positioning members 41, 42, 43, 44 may fulfill two functions. The first function is that the heart support device can be inserted in the heart lumen 13 by expanding it from a collapsed state to an expanded state. The second function is to provide circulatory assistance by cyclically inflating and deflating the internal member 9 with a fluid supplied to and retrieved from the dynamic member 9 through the catheter 40 and the one or more positioning members 41, 42, 43, 44.

As with the embodiments shown in FIGS. 9 and 10, the one or more positioning members 41, 42, 43, as well as the ring shaped member 44, are adapted to follow internal curvatures and match internal surfaces of the heart lumen 13 in which the heart support device is placed. However, any interference with internal heart structures that are necessary for proper functioning of the heart is avoided. Examples of such internal structures are papillary muscles and/or chordea tendineae, which should be able to freely operate when the heart support device is in operation in the heart lumen 13. During circulatory assistance, the catheter 40 may extend through a heart valve with minimal interference with the heart valve cusps. The catheter 40 enables the supply and retrieval of a fluid without the need to pass through a hole in a heart wall.

In the embodiments described above, the operation of the internal member 6 with the dynamic volume body may be accomplished by proper supply of a fluid as described above, wherein the fluid may be a suitable liquid or a gas.

The present invention embodiments have been described above with reference to a number of exemplary embodiments as shown in and described with reference to the drawings. Modifications and alternative implementations of some parts or elements are possible, and are included in the scope of protection as defined in the appended claims.

The invention claimed is:

1. Heart support device for circulatory assistance, comprising an internal member to be disposed inside a heart lumen and having a dynamic volume body, the internal member having a substantially stiff wall strengthening portion arranged to engage an inner wall surface of the heart in operation and a dynamic member that is periodically inflatable to assist pumping action of the heart, wherein the wall strengthening portion is expandable.

2. Heart support device according to claim 1, wherein the wall strengthening portion comprises an inflatable cup shaped body.

3. Heart support device according to claim 1, wherein the internal member further comprises one or more positioning members.

4. Heart support device according to claim 1, wherein the internal member is attached to a catheter.

5. Heart support device according to claim 1, wherein the wall strengthening portion comprises an inflatable base chamber configured for expanding a base portion of the wall strengthening portion into a static inflated state in the heart lumen.

6. Heart support device according to claim 5, wherein the base chamber of the wall strengthening portion is inflatable with a liquid medium, a gel, or a powder.

7. Heart support device according to claim 1, wherein the dynamic member comprises a stretchable membrane forming a balloon chamber.

8. Heart support device according to claim 7, wherein the stretchable membrane is hermetically attached to the wall strengthening portion along a circumferential portion thereof, the stretchable membrane and the wall strengthening portion forming the balloon chamber.

9. Heart support device according to claim 7, wherein the stretchable membrane is a substantially spherical membrane in an inflated state.

10. Heart support device according to claim 7, wherein the stretchable membrane comprises an elastic cloth.

11. Heart support device according to claim 7, wherein the stretchable membrane comprises a titanium netting.

12. Heart support device according to claim 1, further comprising a pumping device in communication with the internal member.

13. Heart support device according to claim 1, further comprising an external shell element having a support surface of a rigid material, and being arranged to engage an outer wall surface of the heart.

14. Heart support device according to claim 13, wherein the external shell element comprises a circumferential overlap region.

15. Heart support device according to claim 13, wherein the wall strengthening portion comprises a circumferential overlap region.

16. Heart support device according to claim 13, further comprising a first tubular member connecting the external shell element and the wall strengthening portion, the first tubular member being in communication with the dynamic member.

17. Heart support device according to claim 13, wherein the external shell element comprises a substantially non-resilient bowl-shaped geometry.

18. A system comprising:

the heart support device according to claim 1; and a delivery device arranged for delivering the heart support device in a collapsed state, comprising a central conduit attachable to a surface of a heart wall at a distal end, and a first conduit and a second conduit attached to the central conduit at a proximal end.

* * * * *